(12) United States Patent
Sherwin

(10) Patent No.: US 7,104,657 B2
(45) Date of Patent: Sep. 12, 2006

(54) LENS PROTECTION FOR MEDICAL PURPOSES

(75) Inventor: Daniel Sherwin, Jerusalem (IL)

(73) Assignee: Spintech Med. Ltd. (GI)

( * ) Notice: Subject to any disclaimer, the term of this patent is extended or adjusted under 35 U.S.C. 154(b) by 263 days.

(21) Appl. No.: 10/204,393

(22) PCT Filed: Feb. 20, 2001

(86) PCT No.: PCT/IL01/00158

§ 371 (c)(1),
(2), (4) Date: Dec. 2, 2002

(87) PCT Pub. No.: WO01/61408

PCT Pub. Date: Aug. 23, 2001

(65) Prior Publication Data

US 2003/0137752 A1 Jul. 24, 2003

(30) Foreign Application Priority Data

Feb. 20, 2000 (IL) .................................................. 134630
Nov. 15, 2000 (WO) ................................ PCT/IL00/00750

(51) Int. Cl.
G03B 11/04 (2006.01)

(52) U.S. Cl. ....................................... 359/511; 359/819
(58) Field of Classification Search ................. 359/511, 359/808, 810, 811, 819, 822, 830
See application file for complete search history.

(56) References Cited

U.S. PATENT DOCUMENTS

| 3,879,742 A | | 4/1975 | Smith |
| 4,039,246 A | | 8/1977 | Voigt |
| 4,148,551 A | | 4/1979 | MacAnally |
| 4,497,550 A | | 2/1985 | Ouchi et al. |
| 4,957,112 A | * | 9/1990 | Yokoi et al. ................. 600/463 |
| 5,223,880 A | | 6/1993 | Rapp |
| 5,289,445 A | * | 2/1994 | Luecke .................... 369/44.15 |
| 5,315,333 A | | 5/1994 | Nash |
| 5,505,407 A | | 4/1996 | Chiappetta |
| 5,708,859 A | | 1/1998 | Tajima et al. |
| 5,721,639 A | | 2/1998 | Aoshima et al. |
| 6,000,805 A | | 12/1999 | Inagaki |
| 6,317,279 B1 | | 11/2001 | Chiang |

FOREIGN PATENT DOCUMENTS

| AU | 1507495 | 10/1996 |
| FR | 2 745 170 | 8/1997 |
| JP | 04039443 | 2/1992 |

* cited by examiner

*Primary Examiner*—Euncha P. Cherry
(74) *Attorney, Agent, or Firm*—Fenster & Company

(57) ABSTRACT

A low profile medical lens protector (100) for a medical viewing device having a given diameter, comprising: a rotatable view-through element; a motor which rotates said view-through element; and a housing (140) enclosing said view-through element and said motor, characterized in that said housing has an outer diameter less than 10 mm greater than said given diameter.

33 Claims, 4 Drawing Sheets

LENS PROTECTION FOR MEDICAL PURPOSES

RELATED APPLICATIONS

This application is a U.S. national filing of PCT Application No. PCT/IL01/00158, filed on Feb. 20, 2001. This application is also related to PCT Application No. PCT/IL00/00750, filed on Nov. 15, 2000, the disclosure of which is incorporated herein by reference.

FIELD OF THE INVENTION

The present invention is related to the field of protection of viewing devices from interference, especially by means of centrifugal lens protectors.

BACKGROUND OF THE INVENTION

Various optical systems are required to operate in adverse environments, in which various solid particles and/or fluid droplets etc. and/or other agglomerations of one or more materials of various stickiness or viscosity (herebelow collectively termed "debris") may adhere to the lens and reduce image quality.

One solution is a centrifugal lens protector, in which a spinning glass disc is placed before the lens, so that all the particles are intercepted by the disc. The centrifugal force generated by the disc as it rotates throws the particles towards the circumference of the disc, where they fall off and/or otherwise stop interfering with the image.

U.S. Pat. No. 5,223,880 to Rapp, the disclosure of which is incorporated herein by reference, describes a camera protector in which the disc is integrated with a rotor of a magnetic motor, with a casing surrounding the disc being the motor housing.

U.S. Pat. No. 5,315,333 to Nash, the disclosure of which is incorporated herein by reference, provides a single motor coupled to the disc using a band. The disc is mounted on two lines of bearings. The lens protection device is mounted on the camera, to isolate lens from gyroscopic and vibration forces.

Australian application 9515074, the disclosure of which is incorporated herein by reference, describes another band-based system, in which the disc is said to rotate at between 2600 and 3000 RPM. It is suggested to use a curved or hydrophobic surface to assist in water removal. The motor can be powered using the camera battery pack or using a separate battery.

A particularly difficult environment to view is the inside of the human body. Various medical instruments have been devised for this purpose, for example: the endoscope, the laparoscope which is used for treatment, for example surgery or cauterization or alternative methods of treatment. Commonly an endoscope lens becomes at least partially occluded by body fluids and particles, becoming inoperative. In such circumstance the lens must cleaned. One method of cleaning the lens is to stream a jet of water at the lens, the stream coming from a tube which generally is an integral part of the endoscope assembly. Sometimes the endoscope must be withdrawn for cleaning and reinserted, a time-consuming, risk-increasing and often uncomfortable procedure.

SUMMARY OF THE INVENTION

An aspect of some embodiments of the present invention relates to a centrifugal lens protector, for medical viewing devices. In an exemplary embodiment of the invention, the protector comprises a transparent view-through element, which is fixed to a part of a motor. Optionally, the motor is co-axial with the view-through element. In an exemplary embodiment of the invention, the motor is an electric motor, optionally brushless, and the view-through element is integral with the rotor of the motor, e.g., having a plurality of magnets fixed thereon. Possibly, a housing of the protector forms the stator. In an exemplary embodiment of the invention, the housing is used to couple the protector to the viewing device or is integral with the viewing device. In an alternative embodiment, the motor is an electrostatic motor, with the magnets being replaced by electrostaticly charged elements.

In an exemplary embodiment of the invention, the magnets extend axially for a considerable distance away from the view-through element, possibly being contained in a cylinder defined by the view-through element, or extending out radially by a small amount. In an exemplary embodiment of the invention, the motor defined by the magnets is hollow, to receive the tip of the viewing device. Alternatively, neither the magnets nor the coils enclose the viewing device. Optionally, the poles of the magnets are axially oriented.

In an exemplary embodiment of the invention, the lens protection element does not significantly add to the diameter of an entrance aperture of the viewing device, while not substantially blocking viewing ability of the device, for example, by being axially disposed relative to the viewing device. For example, the diameter of the aperture may remain the same, or be increased by less than 50%, less than 40%, less than 30% or even less than 10%. For example, the outer diameter may be increased by less than 5 mm, less than 3 mm, less than 2 mm or less than 1 mm. In an exemplary embodiment of the invention, the housing diameter and/or sheath diameter are selected to match standard endoscope conveying tube diameters.

Exemplary medical viewing devices include invasive medical devices, such as viewing or tool carrying endoscopes, laparoscopes and catheters, which devices may be flexible or rigid and non-invasive devices, such as surgical microscopes and magnifying goggles or glasses attachments.

The view through element may be optically inactive, e.g., being a transparent disc, flat or convex, or active, for example, being a lens (e.g., instead of or in addition to a lens of the viewing device) or a filter.

In an exemplary embodiment of the invention, the lens protector is provided integral with the viewing device, for example, being encased in a same tube as the viewing device and/or replacing the outermost optical element of the viewing device. Alternatively, the lens protector is provided as an add-on. The add-on may be merely attached to the end of the viewing device, optionally, with control wires leading to the other end of the device. Alternatively, the add-on may comprise a sheath that encases the viewing device. The sheath optionally includes one or more channels, for example, for providing lens cleaning fluid, one or more light sources, vacuum and/or tools. Optionally, the channels are elastically compressible towards the viewing device, when not in use. Alternatively or additionally, the lens protector includes at least one aperture for alignment with at least one tool-channel of the viewing device.

An aspect of some embodiments of the present invention relates to a contact-sensitive lens protector. In an exemplary embodiment of the invention, the view-through element stops rotating when it contacts a surface, for example a membrane in the body, for example, to prevent inadvertent damage to body tissues. In an exemplary embodiment of the invention, the lens protector is provided with enough power to generate a torque that can sustain substantially free rotation, but not with enough power to re-start the rotation once it has stopped. In an exemplary embodiment of the invention, a control box includes a restart-button, for sending a power surge to the lens protector, so that it can be restarted.

In an exemplary embodiment of the invention, the lens protector is packed with a power supply (e.g. a battery) that once turned on, can operate only for a limited amount of time, for example, between 5 minutes and two hours. After that time, the power supply runs out and cannot be replaced without damaging the lens protector.

There is thus provided in accordance with an exemplary embodiment of the invention, a low profile medical lens protector for a medical viewing device with an entrance aperture having a given diameter, comprising:

a rotatable view-through element which does not block said entrance aperture;

a motor which rotates said view-through element; and a housing enclosing said view-through element and said motor, characterized in that said housing has an outer diameter less than 10 mm greater than said given diameter. Optionally, said outer diameter is less than 5 mm greater than said given diameter. Optionally, said outer diameter is less than 2.1 mm greater than said given diameter.

In an exemplary embodiment of the invention, said view-through element is integral with a rotor of said motor. Alternatively or additionally, said housing is integral with a stator of said motor. Alternatively or additionally, said housing has a flared rim.

In an exemplary embodiment of the invention, said motor is a magnetic motor. Optionally, said motor comprises a plurality of axially disposed magnets, attached to said view-through element. Optionally, the protector comprises at least one tension ring preventing radial motion of said magnets. Optionally, said motor comprises a magnetic ring, attached to said view-through element.

In an exemplary embodiment of the invention, said motor comprises a hollow rotor. Optionally, the protector comprises at least two axially displaced bearings coupling said rotor to said housing. Optionally, said at least one of said bearings is a slip ring bearing. Optionally, said at least one of said bearings is rotating bearing. Alternatively or additionally, said bearings are at either end of said housing.

In an exemplary embodiment of the invention, the protector comprises a power source that provides only enough power to said motor to maintain said view-through element in rotation and not to initiate rotation. Optionally, said power source is operative to provide a power surge sufficient to initiate rotation of said view-through element.

In an exemplary embodiment of the invention, said viewing device comprises an invasive viewing tube device. Optionally, said viewing tube is flexible. Alternatively or additionally, said protector is adapted to attach to said viewing tube. Optionally, said protector is attached to said tube substantially only at a proximal part of said protector, distal from said view-through element. Alternatively, the protector comprises a sheath adapted to fit on said viewing tube. Optionally, said sheath defines at least one axial tube.

In an exemplary embodiment of the invention, the protector comprises a short sleeve for coupling said protector to said viewing tube.

In an exemplary embodiment of the invention, said protector is integral with said viewing tube.

In an exemplary embodiment of the invention, said viewing tube comprises at least one work channel and wherein said protector comprises at least one tube extension that can be aligned with said channel.

In an exemplary embodiment of the invention, said view-through element rotates at at least 5,000 r.p.m. Alternatively or additionally, said view-through element rotates at at least 10,000 r.p.m. Alternatively or additionally, said view-through element rotates at at least 20,000 r.p.m.

In an exemplary embodiment of the invention, said protector has an outer diameter of less than 30 mm. Alternatively or additionally, said protector has an outer diameter of less than 20 mm. Alternatively or additionally, said protector has an outer diameter of less than 7 mm.

BRIEF DESCRIPTION OF THE DRAWINGS

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear. Dimensions of components and features shown in the figures are chosen for convenience and clarity of presentation and are not necessarily shown to scale.

DETAILED DESCRIPTION OF SOME EMBODIMENTS

Figure 1:
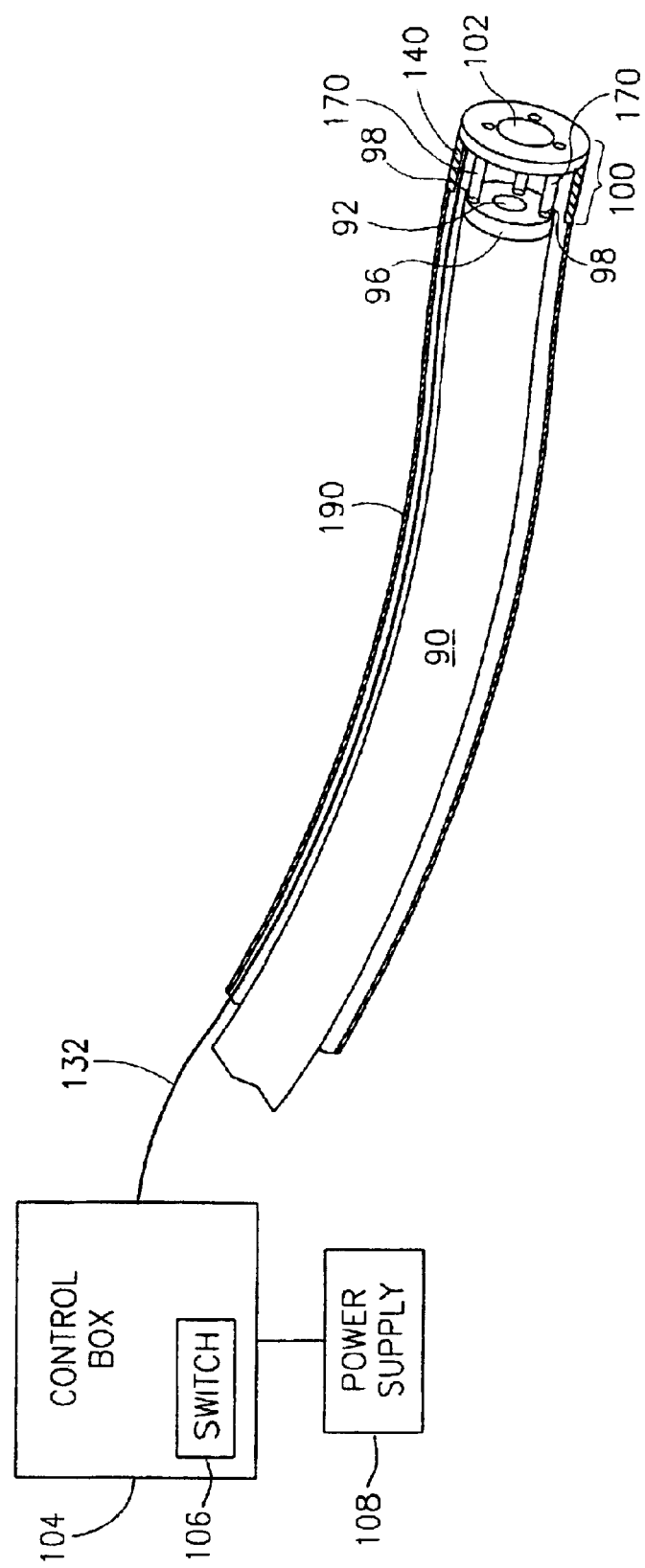
FIG. 1 is a schematic view of a lens protector with a sheath enclosing an endoscope, in accordance with some embodiments of the present invention.

FIG. 1 is a oblique schematic view of the inserted end of an endoscope 90, with its head covered by a centrifugal lens protector 100, in accordance with some embodiments of the present invention. (The distance between lens protector 100 and the head of endoscope 90 is exaggerated for clarity.)

At the front of endoscope 90 is a lens 92, held in a housing 96. Optionally one or more tubes 98 pass through housing 96. Tubes 98 may be used for a variety of functions, for example, for pumping gas into the volume to be viewed, to suck fluids and particles out from the volume, to spray water for example to clean an area to be viewed or to clean endoscope lens 92, to provide light, to provide therapeutic materials and/or to provide tools. The sizes and number of tubes 98 may vary between endoscopes. Different lens protectors may be provided for different sized and configured endoscopes.

Lens protector 100 is affixed at the front of endoscope 90. A disc 102 (or a curved plate or a lens or a filter) covers endoscope lens 92, and optional tube extensions 170 cover the endings of tubes 98, continuing the tube through lens protector housing 140.

In an exemplary embodiment of the invention, protector 100 comprises a short sleeve (not shown) that mounts on the end of endoscope 90, for example, using pressure (e.g., being elastic or including a tension band) or an adhesive. Optionally, the short sleeve includes a tear string for fast removal from the endoscope. Alternatively, protector 100 includes one or more extensions (not shown) that fit into endoscope tubes. Alternatively, for some types of endoscopes, protector 100 fits on existing mounting locations of the inserted end of the endoscope.

In one embodiment, protector 100 fits to the end of endoscope 90. Alternatively, endoscope 90 (or another type of viewing element) is provided through a larger tube and protector 100 is fixed to that tube. Wires for the protector may be provided through the outer tube. Alternatively, the protector is attached to the viewing device itself, even if the device is provided through an outer tube.

In an exemplary embodiment of the invention, a motor portion of protector 100, that rotates disc 102, extends between 2 mm and 20 mm, for example, 7.5 mm or 15 mm. For example, the length of the motor portion may be comparable to the diameter of endoscope 90 or even be greater. The short sleeve may be, for example, between 2 and 30 mm long, for example, 10 mm or 20 mm. Alternatively, an inner compression ring is provided inside protector 100, to engage the endoscope. The disc is optionally thin, for example, less than 1 mm or less than 0.5 mm.

In an alternative embodiment of the invention, protector 100 comprises a sheath 190 that encloses endoscope 90. Sheath 190 may be integral with protector 100 or it may by attached to the protector after manufacture, for example, being fit over the protector when mounting the protector on the endoscope. An optional control box 104 controls the activities of lens protector 100 via one or more leads 132 that extend from lens protector 100 to lens protector control box 104. As noted above, leads 132 may pass through endoscope 90. Alternatively, leads 132 are embedded in the sheath or lie between the sheath and endoscope 90. Box 104 optionally includes a band or an adhesive backing for attachment to a handle (not shown) of endoscope 90.

Optionally, sheath 190 is sealed to housing 140 in a water-tight seal, which may reduce the risk of contamination and the need for sterilizing of the endoscope itself (e.g., with the sheath being sterile and disposable). Optionally, sheath 190 comprises a plurality of rings, to better seal the endoscope against an outer conveying tube, e.g., for applications where the endoscope is in a pressurized environment. Sheath 190 optionally includes one or more tubes, for example, for control elements, suction and pressure for lens protector 100. In an exemplary embodiment of the invention, sheath 190 comprise a fixed plate between endoscope 90 and disc 102, to prevent contaminants from reaching the endoscope through the disc area. A plurality of valve-openings are optionally defined in the disc, for example, for passing tubes therethrough.

Figure 2:
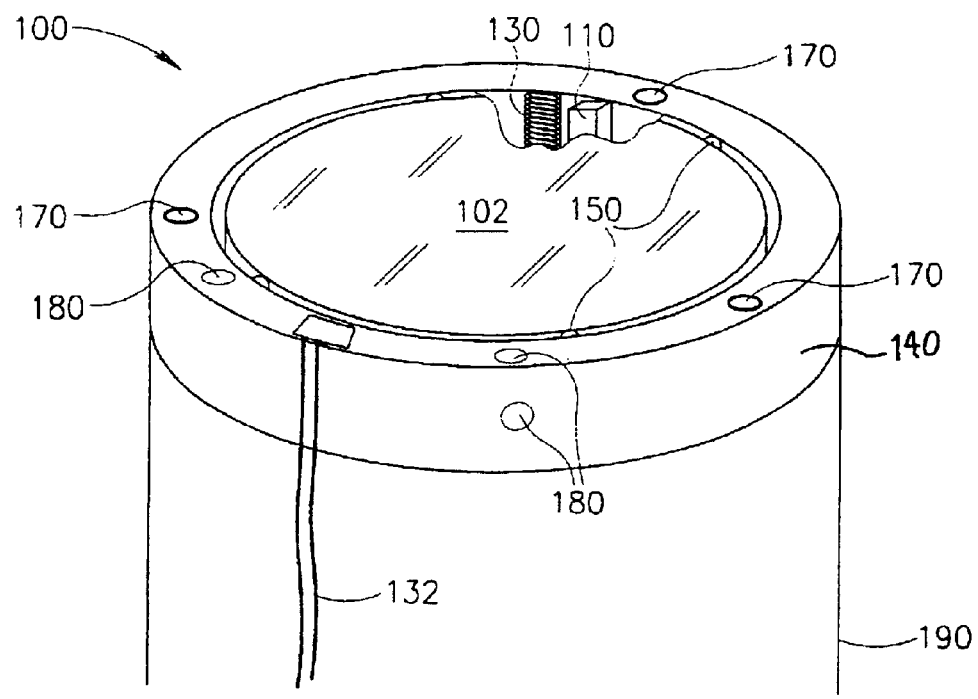
FIG. 2 is a schematic enlarged view of a lens protector in accordance with some embodiments of the present invention.

FIG. 2 is an oblique schematic view of centrifugal lens protector 100, in accordance with some embodiments of the present invention. A substantially transparent disc 102 is provided, which is held in housing 140 in such a way as to enable disc 102 to rotate freely, as described, for example, below. Housing 140 attaches to the inserted end of endoscope 90.

Housing 140 is optionally provided with a plurality of extensions 170, which are a continuation of tubing 98. Some passageways may be used for suction, to remove fluids or particles from the environment of disc 102. In some embodiments of the invention, housing 140 is provided with depressions or cavities 180 which act as receptacles or attachment points for instruments. In some embodiments some cavities 180 may be located inside extensions 170. One or more of extensions 170 may be used for control wires connecting to instruments outside the endoscope, for example instruments held in cavities 180. Optionally, some passageways are used for more than one function.

Figure 3:
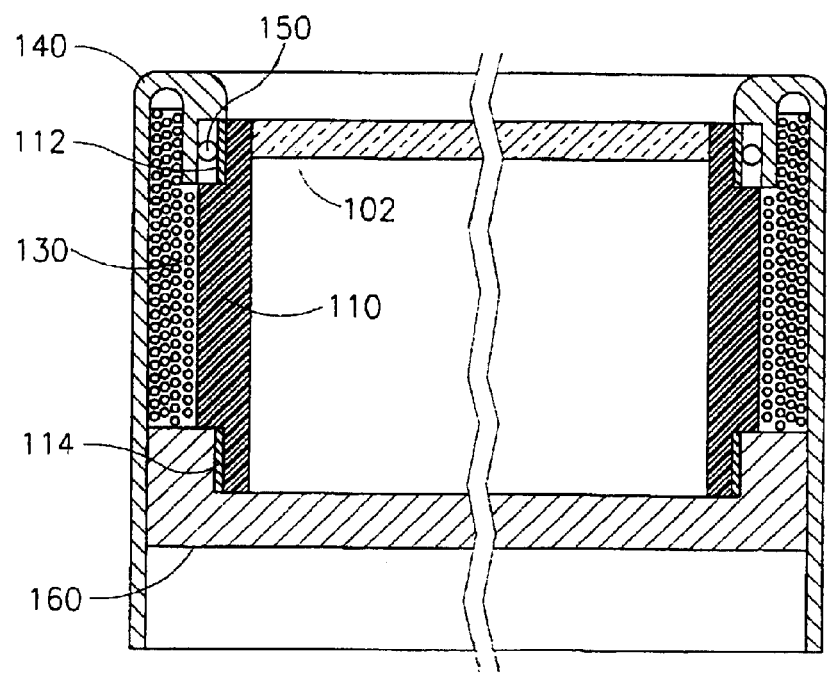
FIG. 3 is a schematic view of a section through a disc-rotor, two of its magnets and its housing-stator, in accordance with some embodiments of the present invention.

FIG. 3 is a cut-through illustration of FIG. 2. Disc 102 is provided with a plurality of axially aligned magnets 110. One end of each magnet is affixed to disc 102, for example using an adhesive or using a tension ring surround the magnets. Optionally, the magnets are mounted directly on disc 102, for example, being held in depressions formed in disc 102. Magnets 110 extend axially from disc 102 into the volume of housing 140. Disc 102 is optionally held in place by a plurality of ball or cylinder bearings 150, which enable rotation. In some embodiments the diameter of a bearing 150 is 0.2 millimeter. Alternatively or additionally, a slip-ring bearing is used. At the base of protector 100, a second bearing 160 is optionally provided, for example, a slip-ring bearing.

In an exemplary embodiment of the invention, magnets 110 are interconnected by a pair of optional sliding rings 112 and 114 which serve, as tension rings, to prevent the centrifugal force of rotation from detecting the magnets from disc 102 or causing undue distortion. Sliding rings 112 and 114 slide in contact with bearings 160 and 150. In some embodiments of the invention, the life time of protector 100 is relatively short, so wear of the bearings is not crucial. Such slip rings may be mounted on the moving part (e.g. the disc) or on the static part (e.g., housing 140).

In an exemplary embodiment of the invention, the bearings are loose and server merely to assists the initiation of rotation of disc 102. After the initiation, air currents may prevent disc 102 from contacting housing.

Optionally, magnets 110 and/or the inner surface of disc 102 include bearings or a smooth surface (e.g., with or without a coating), for smoothing contact between the outside of endoscope 90 and the inner surface of protector 100.

A plurality of coils 130 are provided within the body of housing 140, at or close to the inner surface of housing 140. In some embodiments of the invention, coils 130 are fabricated by a process of depositing electroconductive material, e.g. copper or silver or platinum or an electroconductive plastic in an especially formed cavity in housing 140. Many different lithographic methods may be used for fabricating coils 130. Alternatively, the coils are deposited on a rigid or flexible substrate and the substrate is inserted in housing 140.

Alternatively or additionally, coils 130 are wound on cores, optionally ferromagnetic cores. Coils 130, on their cores, are inserted into a receptive depression in housing 140. In some embodiments housing 140 and/or coils 130 and/or the said cores are provided with means of securing coils 130 in position in housing 140, for example, adhesives.

In an exemplary embodiment of the invention, the positioning of the coils is selected so that extensions 170 can pass between coils, for example, a specific arrangement of coil locations for each endoscope design.

In an exemplary embodiment of the invention, the coils are wound on housing 140 in a three phase air coil skew coreless coil, in which each winding encircles the housing, with its axial position varying from one axial end of the housing to the other and back, during a circuit. In an exemplary embodiment of the invention, the wire used is between 0.05 mm and 0.12 mm and the length of wire for each phase is about 3.2 m. The final thickness of the windings is, for example, 0.2 mm.

Current supply to coils 130 is controlled by lens protector control unit 104, which optionally comprises an electronic brushless commutator (not shown), for example a Philips TDA1540AT. A plurality of leads 132, which in some embodiments may at least partially be comprised of wires, lead from control box 104 to coils 130. Changes of electric current in coils 130 generate varying magnetic fields which act on magnets 110, causing disc 102 to rotate, as well known in the art of magnetic motors. In various embodiments of the present invention the steady rate of rotation of lens protector 100 lies between 2000 r.p.m. and 40,000 r.p.m, for example, more than 5,000 r.p.m. or more than 20,000 r.p.m., or any suitable intermediate speed.

To illustrate an exemplary embodiment of the present invention, FIG. 3 shows diametrically opposite magnets and coils, at an instant in which the magnets are in close proximity to coils 130. In such position the actual gap between coils 130 and magnets 110 in some embodiments is smaller than 0.2 mm, for example being as small as 0.01 mm. Similar gaps are provided between magnets 110 and endoscope 90 (on the inside of protector 100). In some embodiments of the invention coils 130 are arranged not to be diametrically opposite, for example where there is an odd number of coils, for example three coils, at angular intervals of 120 degrees. The number of magnets 110 (e.g., 2, 3, 4, 6 or any larger, smaller or intermediate number) is not necessarily equal to the number of coils 130 (e.g., 2, 3, 4, 6 or any larger, smaller or intermediate number).

In some embodiments of the invention, magnets 110 are electromagnets rather than permanent magnets as in other embodiments. Alternatively to lead based power conduction, in an alternative embodiment of the invention, disc 102 is powered by an induced electric filed, for example, using a AC magnetic field generator or an RF field which are received by an antennas (not shown) on housing 140, as known in the art. Alternatively, the external power source comprises a rapidly rotating magnet, which directly causes disc 102 to rotate.

Alternatively to using an electromagnetic motor, a fluid motor, for example pneumatic (e.g., using air) or hydraulic (e.g., using saline solution) may be used. The pressurized fluid, which may be available via endoscope 90 for performing the procedure, is optionally directed at a plurality of fins attached to disc 102 (corresponding to magnets 110) or at depressions in the circumference of disc 102, thereby causing the disc to rotate.

Bearings 150 and bearings 160, if of ball or of cylinder type, rotate in the opposite direction to the rotation of disc 102, thus the gyroscope effects of bearings 150 and 160 are in the opposite direction as the gyroscope effect of the rotation of disc 102. In some embodiments, to increase the offset of the gyroscope effect of rotating disc 102, bearings 150 and/or bearings 160 are designed to increase their gyroscope effect, for example by manufacturing them of high density materials, by extending the bearings axially, and/or by increasing the number of bearings used.

Figure 5:
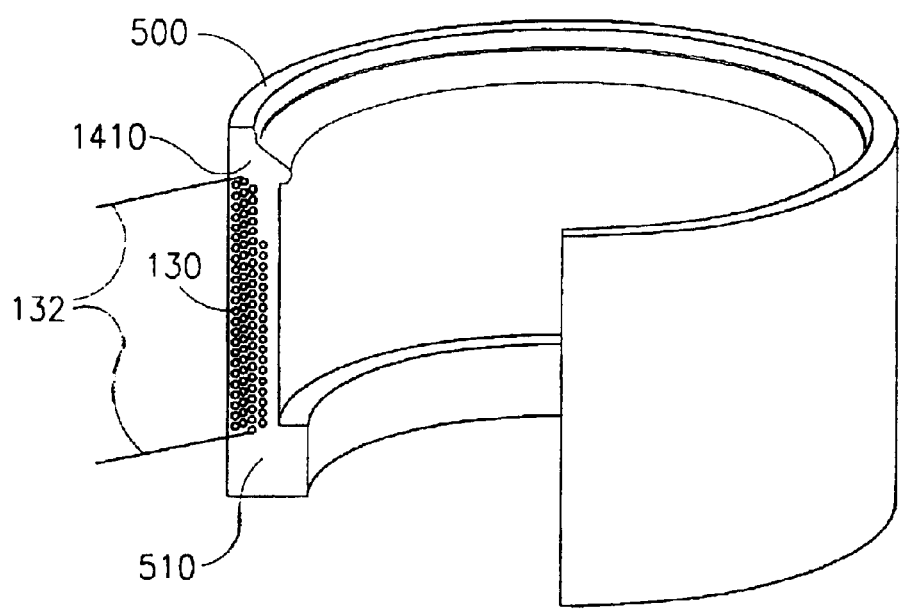
FIG. 5 is a schematic oblique cross-sectional view of a housing for a one-moving piece lens protector in accordance with an exemplary embodiment of the present invention.

Debris which reaches disc 102 is given a centrifugal acceleration by disc 102, and reach a rim 1410 (FIG. 5) of housing 140 with a considerable velocity. As shown in FIG. 5 below, rim 1410 of housing 140 is optionally shaped, e.g., flared, to divert the debris away from the plane of disc 102.

Referring back to FIG. 1, control box 104 optionally includes a switch 106. In some embodiments switch 106 has three positions: OFF, ON, and RESTART. In some embodiments of the invention only two positions are provided: ON and RESTART. In an exemplary embodiment of the invention, once the protector is turned on, the protector can operate only for a fixed amount of time, for example, 10 minutes, 1 hour or two hours. This forces the use of the protector or the power supply (if detachable) as a disposable unit. In an exemplary embodiment of the invention, a power supply 108 used for protector 100 comprises a battery. Wear of the bearings in such a short time may be less important, allowing a lower cost device to be produced. In an exemplary embodiment of the invention, the protector is provided in a package along with instructions for use and/or an indication of matching endoscopes.

In an exemplary embodiment of the invention, disc 102 is rotated using a low amount of torque, for example, only sufficient to continue rotation, but not sufficient to overcome any real amount of friction or to restart the rotation. This provides a safety feature in case disc 102 touches a sensitive membrane. In an exemplary embodiment of the invention, the RESTART switch is provided to enable a surge of power to be provided to protector 100, so that the torque is sufficient to restart rotation.

Alternatively, the restart surge is provided automatically a short time after the rotation of disc 102 stops. Alternatively or additionally, a periodic surge is provided automatically.

Figure 4:
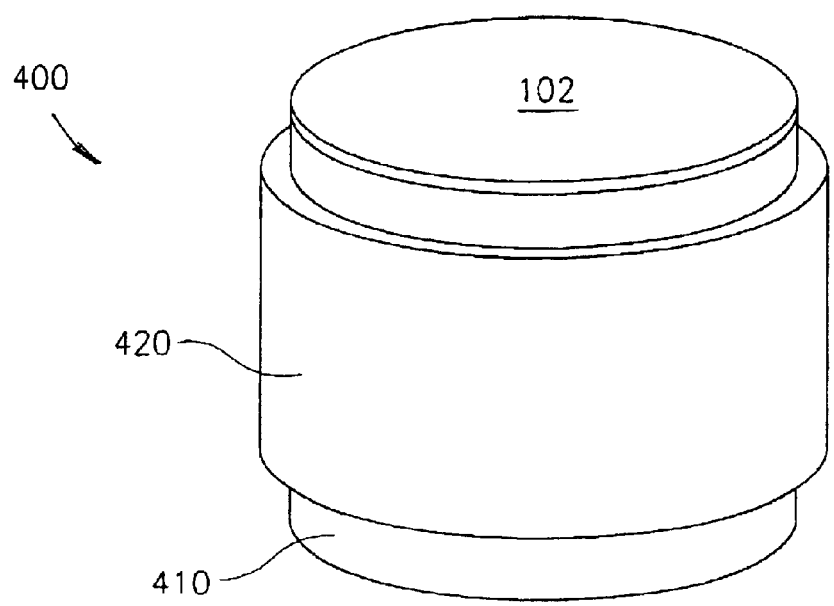
FIG. 4 is a schematic view of the moving part of a one-moving-part lens protector, in accordance with an exemplary embodiment of the present invention.

FIG. 4 is a schematic view of the moving part 400 of a one-moving-part lens protector, in accordance with an alternative exemplary embodiment of the present invention. Part 400 comprises a substantially transparent disc 102, a sleeve shaft 410, and a plurality of radially polarized magnets, fastened together into one mechanical unit on the inside, outside or integral with sleeve shaft 410, as a magnet unit 420. Shaft 410 is optionally in the form of a round hollow tubular cylinder, optionally of thickness 0.05–0.15 millimeter, and is fastened to disc 102, optionally by an adhesive. Magnet unit 420 is made of a magnetizeable material, optionally neotron 666 and is fastened to shaft 410, optionally by an adhesive and optionally polarized in axial strips. The thickness of magnet unit 420 is in some embodiments in the range 0.2 mm–0.8 mm. The diameters and the lengths of shaft 410 and magnet unit 420 and their thickness are determined by the diameter of the lens which the specific lens protector is designed to protect, for example, between 5 mm and 10 mm. In various exemplary embodiments of the invention the length of shaft 410 ranges from 7 millimeter to 20 millimeter and its internal radius ranges between 3 millimeter and 15 millimeter. In various exemplary embodiments of the invention the length of magnet unit 420 ranges from 5 millimeter to 17 millimeter. It should be noted that the design of the coils and the magnets, together with the power level provided, determine the torque that can be achieved.

FIG. 5 schematically shows a cross-sectional view of a housing 500 for the one-moving piece lens protector of FIG. 4, in accordance with an exemplary embodiment of the present invention. Rim 1410 of housing 500 is shaped to divert debris, which were given a centrifugal velocity by disc 102, away from the plane of disc 102. At the opposite side of housing 500 is a rim 510 which holds shaft 410 in a fashion enabling rotation and/or engages the body of endoscope 90. Rim 510 optionally acts as a slider bearing (as bearing 160). Optionally rim 510 is made of a self-lubricating material for example nylon 66, teflon, delarin, okolon, or a polycarbonate. Coils 130 are provided to supply the magnetic fields which cause the rotation of part 400. In some embodiments coils 130 are embedded in the wall of housing 500. Alternatively, coils 130 are fastened thereto. In an exemplary embodiment of the invention, coils 130 comprise elongate rectangular coils. Coils 130 terminate in leads 132, connecting to control box 104 (FIG. 1). In some embodiments of the invention, the connections between coils 130 are in a triangular configuration. Alternatively, a star configuration is used for the connection.

Figure 6:
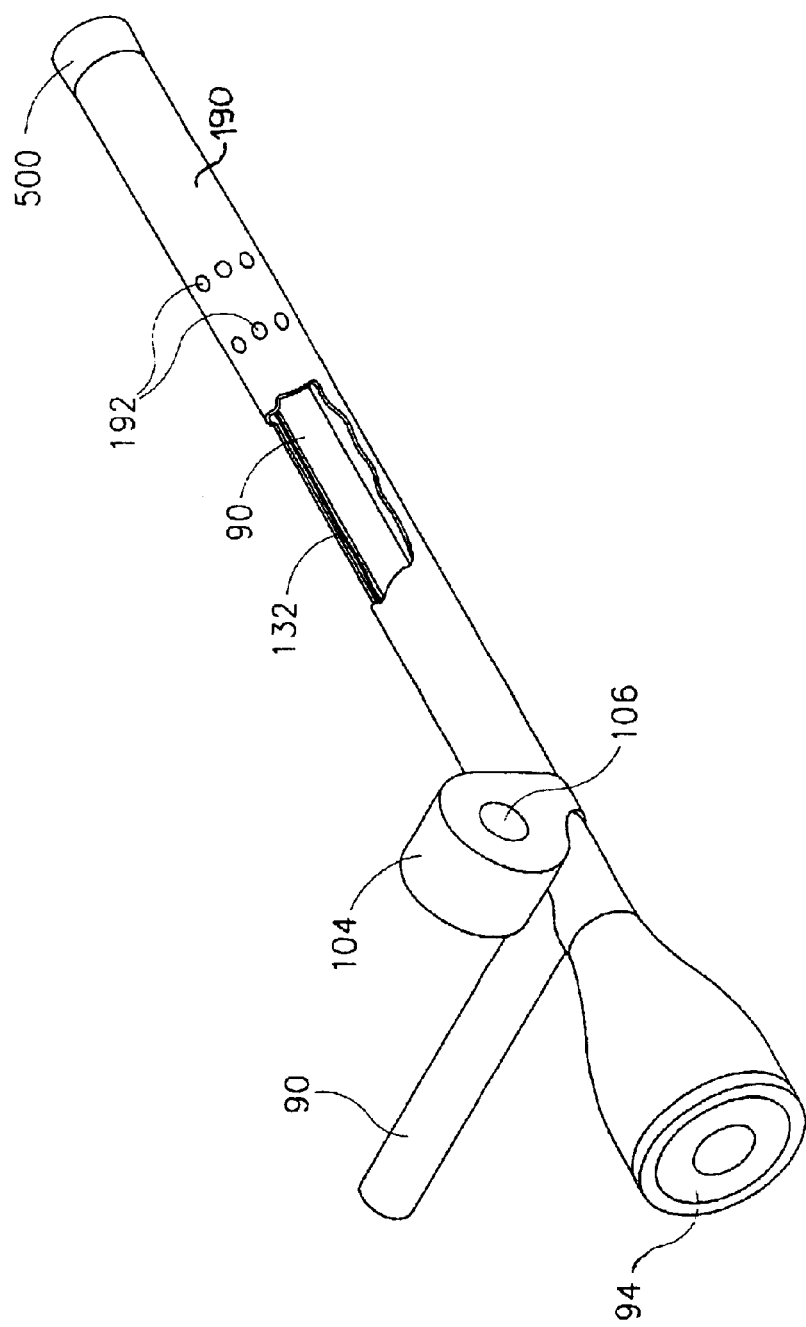
FIG. 6 is a schematic oblique cut-away view of a sheath of a lens protector in accordance with an exemplary embodiment of the present invention.

FIG. 6 is a schematic oblique cut-away view of sheath 190 in accordance with some exemplary embodiments of the present invention. In the embodiment shown, sheath 190 is designed for an endoscope 90. Lens protector 500 is situated at the inserted end of endoscope 90, opposite the endoscope eyepiece 94. Leads 132 are optionally embedded in sheath 190, by any of the techniques well known to a practitioner of the art, optionally with sheath 190 being constructed using one of the techniques known as hollow-tube plastic extrusion.

Endoscope sheath 190 is optionally provided with a pressure balancing mechanism, for example a plurality of holes 192, to prevent a pressure gradient forcing gasses and perhaps carried particles from the inside of the patient into lens protector 100 and into sheath 190.

In some embodiments of the invention sheath 190 is fabricated as an integral part of lens protector 100. In use, endoscope 100 is inserted into sheath 190 until reaching lens protector 100 and there it connects with lens protector 100, optionally by screwing into screw threads at the base of housing 500. Alternatively or additionally, alignment of lens protector 100 is performed with ball and depression arrangements such as click-stops.

Alternatively to being used for an endoscope, a similar lens protector may be constructed to fit a surgical (including ophthalmic) microscope.

A low profile lens protector may also be used for other application, where a high-profile lens protector is not suitable, for example, for field binoculars, sights and laser range finders. In such embodiments the lens protector 100 and it parts will be of the appropriate measurements, which may differ considerably from the measurements mentioned above. Optionally the direction of rotation of the pair of lens protectors for each of the lenses rotates in opposite directions, thus balancing out the gyroscope effect caused by the rotation.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or combinations of features from different ones of the shown embodiments.

The detailed description is provided by way of example and is not meant to limit the scope of the invention, which is limited only by the following claims:

What is claimed is:

1. A low profile medical lens protector for a medical viewing device with an entrance aperture having a given diameter, comprising:
   a rotatable view-through clement which does not block said entrance aperture;
   a motor which rotates said view-through element; and
   a housing enclosing said view-through element and said motor, characterized in that said housing has an outer diameter less than 10 mm greater than said given diameter.

2. A protector according to claim 1, wherein said outer diameter is less than 5 mm greater than said given diameter.

3. A protector according to claim 1, wherein said outer diameter is less than 2.1 mm greater than said given diameter.

4. A protector according to claim 1, wherein said view-through element is integral with a rotor of said motor.

5. A protector according to claim 1, wherein said housing is integral with a stator of said motor.

6. A protector according to claim 1, wherein said housing has a flared rim.

7. A protector according to claim 1, wherein said motor is a magnetic motor.

8. A protector according to claim 7, wherein said motor comprises a plurality of axially disposed magnets, attached to said view-through element.

9. A protector according to claim 8, comprising at least one tension ring preventing radial motion of said magnets.

10. A protector according to claim 7, wherein said motor comprises a magnetic ring, attached to said view-through element.

11. A protector according to claim 1, wherein said motor comprises a hollow rotor.

12. A protector according to claim 11, comprising at least two axially displaced bearings coupling said rotor to said housing.

13. A protector according to claim 12, wherein said at least one of said bearings is a slip ring bearing.

14. A protector according to claim 12, wherein said at least one of said bearings is rotating bearing.

15. A protector according to claim 12, wherein said bearings arc at either end of said housing.

16. A protector according to claim 1, comprising a power source that provides only enough power to said motor to maintain said view-through element in rotation and not to initiate rotation.

17. A protector according to claim 16, wherein said power source is operative to provide a power surge sufficient to initiate rotation of said view-through element.

18. A protector according to claim 1, wherein said viewing device comprises an invasive viewing tube device.

19. A protector according to claim 18, wherein said viewing tube is flexible.

20. A protector according to claim 18 adapted to attach to said viewing tube.

21. A protector according to claim 20, wherein said protector is attached to said tube substantially only at a proximal part of said protector, distal from said view-through element.

22. A protector according to claim 20, comprising a sheath adapted to fit on said viewing tube.

23. A protector according to claim 22, wherein said sheath defines at least one axial tube.

24. A protector according to claim 20, comprising a short sleeve for coupling said protector to said viewing tube.

25. A protector according to claim 20, wherein said protector is integral with said viewing tube.

26. A protector according to claim 18, wherein said viewing tube comprises at least one work channel and wherein said protector comprises at least one tube extension that can be aligned with said channel.

27. A protector according to claim 1, wherein said view-through element rotates at at least 5,000 r.p.m.

28. A protector according to claim 1, wherein said view-through element rotates at at least 10,000 r.p.m.

29. A protector according to claim 1, wherein said view-through element rotates at at least 20,000 r.p.m.

30. A protector according to claim 1, wherein said protector has an outer diameter of less than 30 mm.

31. A protector according to claim 1, wherein said protector has an outer diameter of less than 20 mm.

32. A protector according to claim 1, wherein said protector has an outer diameter of less than 7 mm.

33. A protector according to claim 1, wherein said view-through element is optically transparent.

* * * * *